US007476856B2

(12) United States Patent
Watanabe et al.

(10) Patent No.: US 7,476,856 B2
(45) Date of Patent: Jan. 13, 2009

(54) SAMPLE DIMENSION-MEASURING METHOD AND CHARGED PARTICLE BEAM APPARATUS

(75) Inventors: Kenji Watanabe, Oume (JP); Tadashi Otaka, Hitachinaka (JP); Ryo Nakagaki, Kawasaki (JP); Chie Shishido, Yokohama (JP); Masakazu Takahashi, Tsuchiura (JP); Yuya Toyoshima, Sendai (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 10/875,509

(22) Filed: Jun. 25, 2004

(65) Prior Publication Data

US 2005/0051721 A1 Mar. 10, 2005

(30) Foreign Application Priority Data

Jun. 27, 2003 (JP) .............................. 2003-183715

(51) Int. Cl.
  *G01N 23/00* (2006.01)
  *G01B 11/10* (2006.01)
(52) U.S. Cl. ........................ 250/310; 250/306; 250/307; 250/309; 250/311; 356/388; 356/392; 356/394; 356/636; 356/639; 356/640; 356/393
(58) Field of Classification Search ................. 250/300, 250/306, 307, 309, 310, 311; 356/72, 73, 356/601, 614, 615, 622, 625, 628–630, 634–636, 356/639, 640, 388.39, 392–394
See application file for complete search history.

(56) References Cited

U.S. PATENT DOCUMENTS

| 4,807,159 | A | * | 2/1989 | Komatsu et al. ............ 250/311 |
| 5,336,887 | A | * | 8/1994 | Yagi et al. ................... 250/306 |
| 5,436,448 | A | * | 7/1995 | Hosaka et al. .............. 250/306 |
| 6,515,296 | B1 | * | 2/2003 | Komatsu et al. ........ 250/559.44 |
| 6,538,248 | B1 | * | 3/2003 | Kametani et al. ........... 250/310 |
| 6,567,168 | B2 | * | 5/2003 | Nara et al. ................... 356/394 |
| 6,580,075 | B2 | * | 6/2003 | Kametani et al. ........... 250/310 |
| 6,583,414 | B2 | * | 6/2003 | Nozoe et al. ................ 250/310 |
| 6,594,012 | B2 | * | 7/2003 | Takeuchi et al. ............ 356/394 |

(Continued)

FOREIGN PATENT DOCUMENTS

JP  P2003-148945  5/2003

(Continued)

OTHER PUBLICATIONS

D. Jefferies, "The Recursion Formula", <http://www.ee.surrey.ac.uk/Personal/D.Jefferies/complex98/jd/cx98jd/node4.html>.*

*Primary Examiner*—Bernard E Souw
(74) *Attorney, Agent, or Firm*—McDermott Will & Emery LLP

(57) ABSTRACT

A method and apparatus for efficiently executing two types of measurements with an optical measuring device and a scanning electron microscope are provided. For example, the method and apparatus may execute the following steps: calculating an average of the dimensional values of a plurality of scanned feature objects; and calculating an offset of a dimensional value on the basis of a difference between the calculated average value and the dimensional value of the feature object obtained when the light is irradiated. The offset between measurement values between the optical measuring device and the scanning electron microscope can be determined precisely.

2 Claims, 18 Drawing Sheets

U.S. PATENT DOCUMENTS

| | | | |
|---|---|---|---|
| 6,635,874 B1 * | 10/2003 | Singh et al. | 250/311 |
| 6,650,424 B2 | 11/2003 | Brill et al. | |
| 6,667,806 B2 * | 12/2003 | Yoshitake et al. | 356/399 |
| 6,703,850 B2 * | 3/2004 | Nozoe et al. | 324/751 |
| 6,724,489 B2 * | 4/2004 | Freifeld | 356/601 |
| 6,777,677 B2 * | 8/2004 | Nozoe et al. | 250/310 |
| 6,808,942 B1 * | 10/2004 | Patel et al. | 438/8 |
| 6,879,403 B2 * | 4/2005 | Freifeld | 356/601 |
| 6,986,280 B2 * | 1/2006 | Muckenhirm | 73/104 |
| 7,112,791 B2 * | 9/2006 | Nozoe et al. | 250/310 |
| 2001/0017878 A1 * | 8/2001 | Nozoe et al. | 374/5 |
| 2001/0021020 A1 * | 9/2001 | Nara et al. | 356/394 |
| 2003/0062479 A1 * | 4/2003 | Kametani et al. | 250/310 |
| 2003/0090651 A1 | 5/2003 | Toyoshima et al. | |
| 2003/0168594 A1 | 9/2003 | Muckenhirn | |
| 2003/0213909 A1 * | 11/2003 | Nozoe et al. | 250/310 |
| 2004/0147121 A1 * | 7/2004 | Nakagaki et al. | 438/689 |
| 2005/0006583 A1 * | 1/2005 | Nozoe et al. | 250/311 |
| 2005/0051721 A1 * | 3/2005 | Watanabe et al. | 250/306 |
| 2007/0023658 A1 * | 2/2007 | Nozoe et al. | 250/310 |

FOREIGN PATENT DOCUMENTS

JP    2005017145 A * 1/2005

* cited by examiner

SAMPLE DIMENSION-MEASURING METHOD AND CHARGED PARTICLE BEAM APPARATUS

TECHNICAL FIELD

The present subject matter relates to a sample dimension-measuring method and a charged particle beam apparatus, and more particularly, to a sample dimension-measuring method including measurement that uses an optical measuring device, and a charged particle beam apparatus.

BACKGROUND

A scanning electron microscope called the CD-SEM (Critical Dimension-Scanning Electron Microscope) is used as a means of measuring the line widths of semiconductor circuit patterns. With this apparatus, although the pattern width of a semiconductor circuit pattern at any location can be measured accurately with a high magnification, since such measurement is limited to narrow regions, the measurement needs to be conducted at a number of locations to evaluate the line widths of the patterns existing in a wide range of regions.

Also, since measurement with the CD-SEM is based on plane-like images obtained from an immediately upward direction, the profiles of sections usually cannot be measured during such measurement. For this reason, the sectional profiles of patterns are measured by actually machining the section of a pattern using ion beams or the like, and then observing this section through the CD-SEM or a transmission electron microscope (TEM).

As described above, the SEM-based measurement from an immediately upward direction has posed the problem that since the sample needs to be destroyed for sectional exposure, it is difficult to obtain three-dimensional information. In order to solve this problem, Japanese Patent Laid open No. 2003-148945 (and corresponding US2003/0090651) suggests measuring the three-dimensional shape of a pattern by use of both the SEM and an optical inspection apparatus. The art disclosed in that document is such that: a test pattern is measured in height by being irradiated with light, then in width and contrast by being irradiated with an electron beam, and the height of a pattern is estimated from the obtained contrast by using a correlation.

Optical inspection apparatuses are able to measure sectional shape profiles, and these apparatuses are high in throughput, compared with a scanning electron microscope. The optical inspection apparatus, however, has the problem that compared with a scanning electron microscope, the magnifications at which such measurement is possible are low and measuring accuracy on pattern width and the like is low. As disclosed in Japanese Patent Laid-open No. 2003-148945 ((US2003/0090651), therefore, it could be conceivable that an optical inspection apparatus and a scanning electron microscope could be combined to perform measurements.

SUMMARY

The previous combination of an optical inspection and an electron microscopy, however, lacks measurement accuracy because the two inspection methods have different principles. Then, it poses the problem of a decrease in throughput, since two different measurements are performed.

An object is to provide: a sample dimension-measuring method and apparatus for high accuracy and/or efficiently executing respective two types of measurements with an optical measuring device and a charged particle beam apparatus represented by a scanning electron microscope.

In order to improve measurement accuracy between the two different measurement methods, there are provided a dimension-measuring method and a charged particle beam apparatus implementing the method. A pattern containing a number of feature objects is irradiated with light of a scatterometry-based optical measuring apparatus to measure an averaged dimensional value of feature objects within the pattern. Also, feature objects within the pattern are scanned with a charged particle beam to measure a dimension of each of the scanned feature objects. The dimension-measuring method comprises the steps of: calculating an average value of the dimensional values of the scanned feature objects; and calculating an offset value of a dimensional value on the basis of a difference between the calculated average value and the averaged dimensional value when the light is irradiated.

According to above subject matter, the measurement value obtained by one measurement method which is estimated from the measurement value obtained by the other measurement method, by improving the accuracy of the offset value. For example, it is possible to take an accurate measurement based on merits of two different measurement methods by corresponding results of different methods precisely.

In order to improve a total throughput of measurement, there are provided a dimension-measuring method and apparatus comprising measuring a dimension of a second pattern (e.g. a dummy pattern formed on a scribe line of a semiconductor wafer) other than a first pattern (e.g. a circuit pattern of a die on the semiconductor wafer) by irradiating a light of an optical measuring device to the second pattern. A determination is made as to whether or not the measured dimensional value of the second pattern is within a pre-estimated permissible range. The actual measuring of a dimension of the first pattern is performed by irradiating it with a charged particle beam when the measured dimensional value of the second pattern is out of the range. According to this subject matter, measurement time of the CD-SEM can be reduced by not performing the measurement of a first measurement pattern with the CD-SEM if the second pattern is good.

As another example to improve a total throughput of measurement, there are provided a dimension-measuring method and apparatus comprising measuring a dimension of a second pattern other than the first pattern by irradiating a light of an optical measuring device to the second pattern. A determination is made as to whether the second pattern is good or not based on a range permissible dimensional value for the second pattern when measured by light irradiation, and measuring fewer numbers of dimensions of first patterns when the second pattern is good than when the first pattern is not good. According to this subject matter, measurement time of the CD-SEM can be decreased by reducing the number of measurement points of a first measurement pattern with the CD-SEM.

BRIEF DESCRIPTION OF THE DRAWINGS

The drawing figures depict one or more implementations in accord with the present concepts, by way of example only, not by way of limitations. In the figures, like reference numerals refer to the same or similar elements.

DETAILED DESCRIPTION

Figure 1:
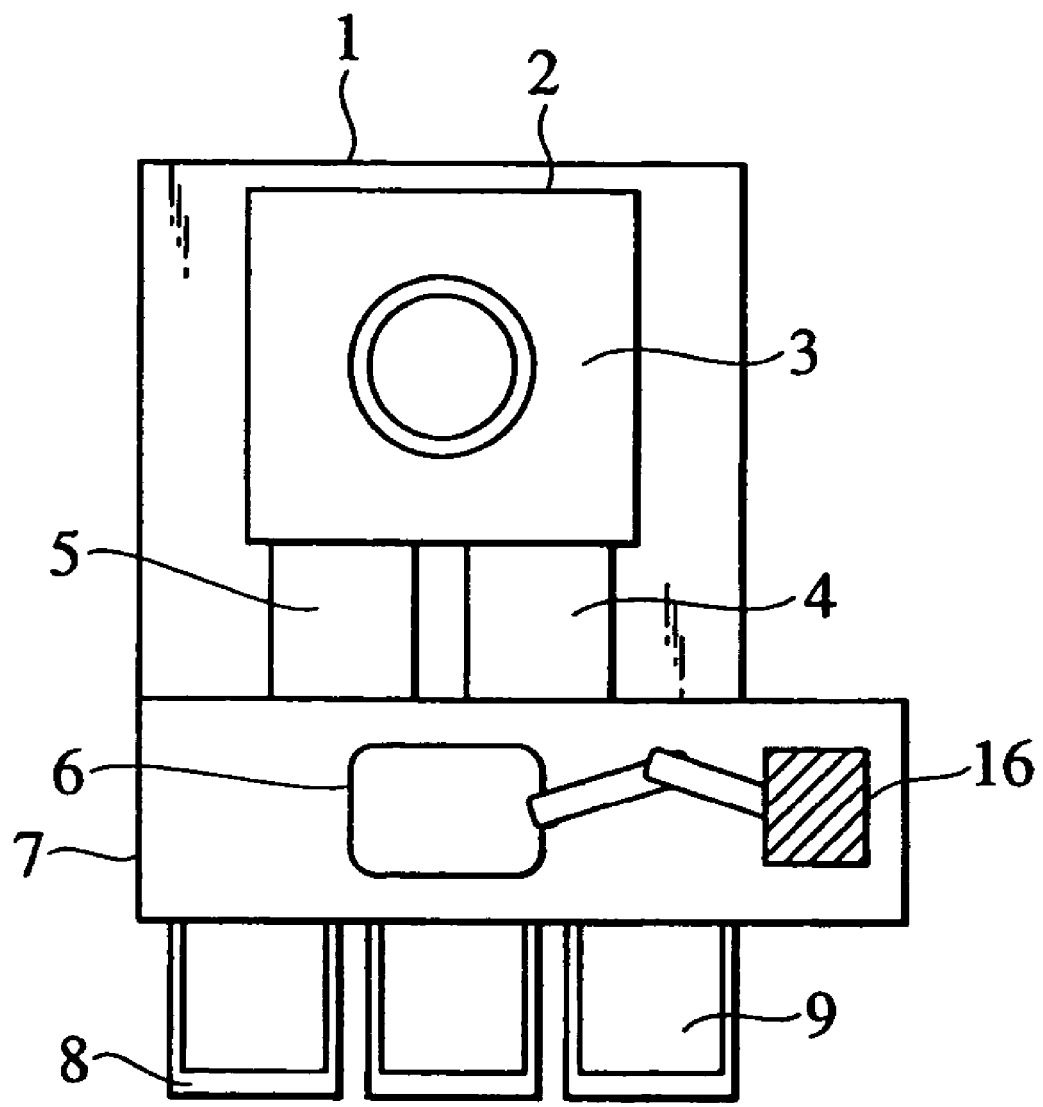
FIG. 1 is a plan view of an integrated-type semiconductor device pattern measuring apparatus.

In an embodiment, a wafer is continuously measured using an optical measuring device example of a scatterometry-based optical pattern shape measuring apparatus. The optical apparatus is mounted as part of a scanning electron microscope for measuring pattern dimensions and shapes of semiconductor devices. The scanning electron microscope may be either a CD-SEM or a review SEM, which allows oblique observation has a function of dimension measuring. During measurements, the scanning electron microscope may be used first and then the scatterometry-based optical pattern shape measuring apparatus, or vice versa.

However, when measuring a photoresist or other materials whose dimensions and the like suffer changes by measurement, it is desirable that light or an electron beam, whichever causes the smaller in the degree of change, should be first used for the measurement. During continuous measurement of one wafer, parallel process steps are carried out in a continuous sequence. More specifically, while a first wafer A, for example, is being measured with the scanning electron microscope first and then with the scatterometry-based optical pattern shape measuring apparatus, a second wafer B is measured with the scanning electron microscope. While an increase in measuring time is minimized, it is possible to obtain both measurements of a first pattern (may also be termed an actual pattern in this Specification, for example a circuit pattern of a die on the semiconductor wafer) using the scanning electron microscope, and measurement of a second pattern (may also be termed a measuring pattern, for example a dummy pattern) using the scatterometry-based optical pattern shape measuring apparatus. Consequently, it becomes possible to measure a greater number of sections within the wafer surface.

During measurement with the scatterometry-based optical pattern shape measuring apparatus, a spectral matching process for a line width and other measurement dimensional values of an object to be measured is also performed allowing for approximate values and a fluctuation range. By measuring these factors beforehand with the scanning electron microscope, it is possible to limit a measuring range of the scatterometry-based optical pattern shape measuring apparatus, hereby to reduce the measuring time, and consequently to measure a greater number of sections.

A measuring pattern is usually disposed in a scribing region of a semiconductor chip, and the measuring pattern is disposed in at least one place per chip. This pattern is measured with the scatterometry-based optical pattern shape measuring apparatus, thus to obtain a profile of a sectional shape. This profile, however, is obtained as an average value of part of the region within the measuring pattern. The scatterometry-based optical pattern shape measuring apparatus can measure the average dimension value of continuous pattern at a time.

As opposed to this, the same measuring pattern is measured with a special scanning electron microscope intended for semiconductor pattern measurement (namely, the Critical Dimension-SEM). Whereas the value that is measured with the scatterometry-based optical pattern shape measuring apparatus is an average value obtained within the measuring pattern region to which a beam of measuring light has been irradiated, a value obtained with the CD-SEM is a value obtained in a very small region. Accordingly, it is necessary to conduct SEM measurements of a plurality of sections within the region of the measuring pattern that was measured with the scatterometry-based optical pattern shape measuring apparatus, and calculate a SEM average value, a variation, and the like, in order to facilitate comparison.

For example, it is possible to take an accurate measurement based on merits of two different measurement methods by corresponding results of different methods precisely.

Since the measuring pattern is disposed in approximately one place per chip, a similar comparative measurement is performed on a plurality of measuring patterns in order to obtain information on a tendency of the entire wafer surface.

Although data measurements on sectional profiles can be obtained using the scatterometry-based optical pattern shape measuring apparatus, only data measurements based on plane-like images, which show widths of a bottom and top of the pattern, can be obtained using the CD-SEM. Accordingly, a corresponding data measurement, for example, the width of the bottom of the pattern, is compared between both apparatuses.

Data measurements obtained at a plurality of sampling positions within the wafer can be easily compared by creating a scatter diagram based on the data measured with the CD-SEM, and from the data measured with the scatterometry-based optical pattern shape measuring apparatus. Furthermore, later correction is possible by creating and utilizing a relational expression between both sets of data by use of a regression formula.

Using the regression formula allows more accurate three dimensional measurement too. For example, at first, measurement control leaves the measuring pattern and shifts to the measurement of a pattern on semiconductor chip. As a result, when the corresponding data measurement, for example, the width of the bottom of the pattern, is obtained, conversion of this value into a value measured with the scatterometry-based optical pattern shape measuring apparatus becomes possible by using the regression formula mentioned earlier in this Specification. Furthermore, a sectional profile of a pattern can be estimated by assuming that a sectional profile of the measuring pattern and that of the pattern are analogous to each other. Otherwise, a sectional profile of the measuring pattern can be estimated on the basis of the assumption that the measuring pattern and the actual pattern are the same in pattern height (i.e., film thickness). A practical method of comparison can be obtained by actually evaluating the above two profiles.

For example, if the above-mentioned regression formula is valid for a certain lot, the sectional profile of the pattern is measurable just by using the formula obtained from a first wafer, and subsequently, performing only measurements with the CD-SEM. If correction needs to be repeated for each wafer, it becomes possible to repeat the above measurement for each wafer, and this means that the measurement can be repeated at the frequency matching a particular situation.

As described above, it is possible to estimate the sectional profile of the pattern by adding the information obtained using the scatterometry-based optical pattern shape measuring apparatus to the information obtained using the CD-SEM.

As another example, a profile of a sectional shape is obtained by measuring a measuring pattern with a scatterometry-based optical pattern shape measuring apparatus similarly to the above. The same measuring pattern is measured using the length-measuring SEM. The processes of performing this series of measurements on a plurality of measuring patterns and creating a relational expression for both by use of a regression formula are performed beforehand.

Unlike measuring patterns, actual patterns inside a semiconductor chip are present in the form of a variety of patterns each varying in line width, pitch, pattern density, shape, and the like. Therefore, it usually cannot be seen beforehand whether, when a particular measuring pattern is already processed into a sectional profile, an actual pattern is also already processed without a problem. In other words, it is difficult to set beforehand the tolerance for, for example, the measured value of a pattern bottom width that is obtained from the measuring pattern.

Therefore, each of the sections that are prone to suffer a defect (such as a wire disconnection, short-circuiting, or a geometric defect) are selected from the actual pattern beforehand and its relationship with the measuring pattern is examined. It is desirable, however, that whether the pattern is nondefective or defective should be judgeable from, for example, a measured value such as pattern width. An actual pattern that was selected for a wafer is measured with the CD-SEM and judgment of whether the actual pattern is nondefective or defective is repeated for a plurality of chips. The measured value mentioned above requires correction using the regression formula obtained beforehand.

Next, the measurements of the measuring pattern that were obtained during the first measurement with the scatterometry-based optical pattern shape measuring apparatus are compared with the results that were obtained by repeating the measurement of the measuring pattern for the plurality of chips.

That is to say, the values that were measured using the scatterometry-based optical pattern shape measuring apparatus are plotted on a horizontal axis, and the measured values corresponding to the selected number of types of actual patterns are plotted on a vertical axis. These values are compared with independently assigned nondefective/defective chip judgment data, and a permissible range of the values measured with the scatterometry-based optical pattern shape measuring apparatus is thereby determined. For more accurate judgment of nondefective/defective chips, a more accurate permissible range can be determined by, for example, during lithography, using the wafers that were exposed under various focal lengths and exposure rates based on a focus exposure map (FEM).

If a measured value greater than the permissible range is detected by an optical pattern shape inspection apparatus, the number of measurement points scanned with the CD-SEM are maintained or increased for measuring circuit patterns precisely to confirm the dimensions of the circuit patterns.

However, if the measurement value obtained by the scatterometry-based optical pattern shape measuring apparatus is within the permissible range, the number of measurement points obtained by the CD-SEM are reduced or maintained, thereby improving a throughput which otherwise would have been limited by using the CD-SEM.

In a case where the number of measurement points is maintained when the measurement value is greater than the permissible range is detected by the optical pattern shape inspection apparatus, the number of measurement points is reduced when the measurement value obtained by the scatterometry-based optical pattern shape measuring apparatus is within the permissible range. In a case where the number of measurement points is increased when the measurement value is greater than the permissible range is detected by the optical pattern shape inspection apparatus, the number of measurement points is maintained when the measurement value obtained by the scatterometry-based optical pattern shape measuring apparatus is within the permissible range.

Although the above explanation explains that the permissible range has an upper permissible value and a lower permissible value, the processing technique is not limited. It is possible to set only the upper permissible value or only the lower permissible value as a boundary determining whether measurement result is good or not.

The measurement times or points may be reduced, if the optical measurements produce good results.

In this way, by determining beforehand a control range corresponding to a product or lot and then immediately only measuring a wafer using the scatterometry-based optical pattern shape measuring apparatus, it becomes possible for nondefective/defective chip judgment of the product pattern to be repeated for a great quantity of chips at high speed.

The above-outlined embodiment of the integrated-type semiconductor device pattern measuring apparatus is described in detail below using the accompanying drawings. First, configurations of a charged particle beam apparatus and an optical pattern shape measuring apparatus used in the present embodiment are described. Although the integrated-type semiconductor device pattern measuring apparatus in the present embodiment is described taking a scanning electron microscope as an example of the charged particle beam apparatus mentioned above, the present embodiment is not limited by this description and can be applied to a length-measuring apparatus that uses an ion beam or other particle beam.

Figure 2:
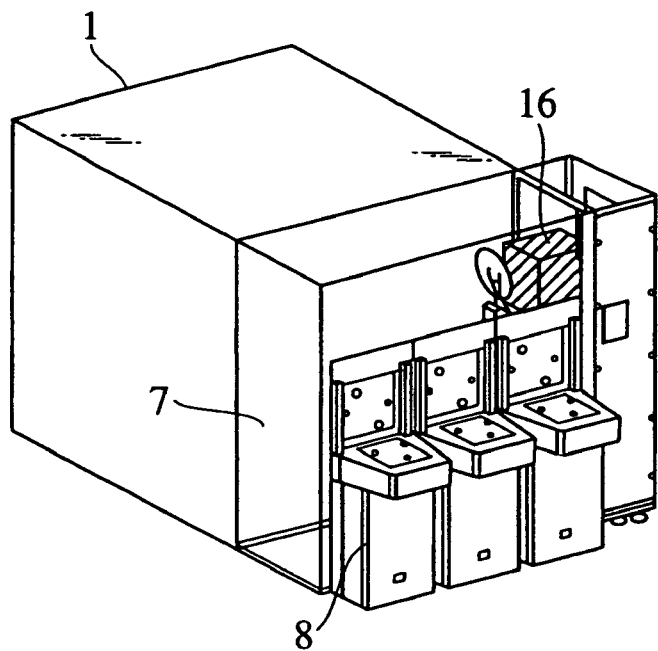
FIG. 2 is a perspective view of the integrated-type semiconductor device pattern measuring apparatus.

FIG. 1 is a plan view of a scanning electron microscope (hereinafter, may be referred to as the CD-SEM) by which the dimensions of a pattern formed on, for example, a semiconductor wafer, are measured on the basis of the electrons (secondary electrons or backscattered electrons) detected when the corresponding sample is scanned in one-dimensional or two-dimensional form by use of the electron beam. FIG. 2 is a perspective view of the CD-SEM.

The CD-SEM shown in FIG. 1 comprises a scanning electron microscope frame 3 and a scanning electron microscope body 1 having a measuring chamber 2 by which a periphery of a sample (such as semiconductor wafer) to be measured is placed in a vacuum atmosphere. Load-lock chambers 4 and 5 for loading and unloading the sample into and from said measuring chamber 2 are connected thereto. The load-lock chambers 4 and 5 are connected to a mini-environment 7, from which the sample is loaded by a transfer robot 6.

The transfer robot 6 operates to retrieve a sample (wafer) from any one of three wafer cassettes 9 and load the sample into the load-lock chamber 4 or 5. Each of the wafer cassettes 9 has a cover not shown in the figure, and this cover is opened by an opener 8 when the sample is retrieved above. Although the present embodiment employs wafer cassettes 9 of the three-port scheme in which three wafer cassettes 9 can be arranged next to one another, the embodiment is not limited by this scheme and may adopt a two-port scheme, for example.

Also, the CD-SEM shown in FIGS. 1 and 2 comprises an optical measuring device 16 (the scatterometry-based optical pattern shape measuring apparatus). The optical shape-measuring device 16 is provided inside the mini-environment 7 and during transfer of a sample, performs the measurements described later. Although, in the present embodiment, the optical shape-measuring device is provided inside the mini-environment 7, the embodiment is not limited by this arrangement and the optical shape-measuring device may be provided inside, for example, the measuring chamber 2 or the load-lock chamber 4 or 5.

In addition, the scanning electron microscope shown in FIGS. 1 and 2 is just an example for explaining the embodiment of the present invention, and can be modified within a range not changing the scope of the invention.

Figure 3:
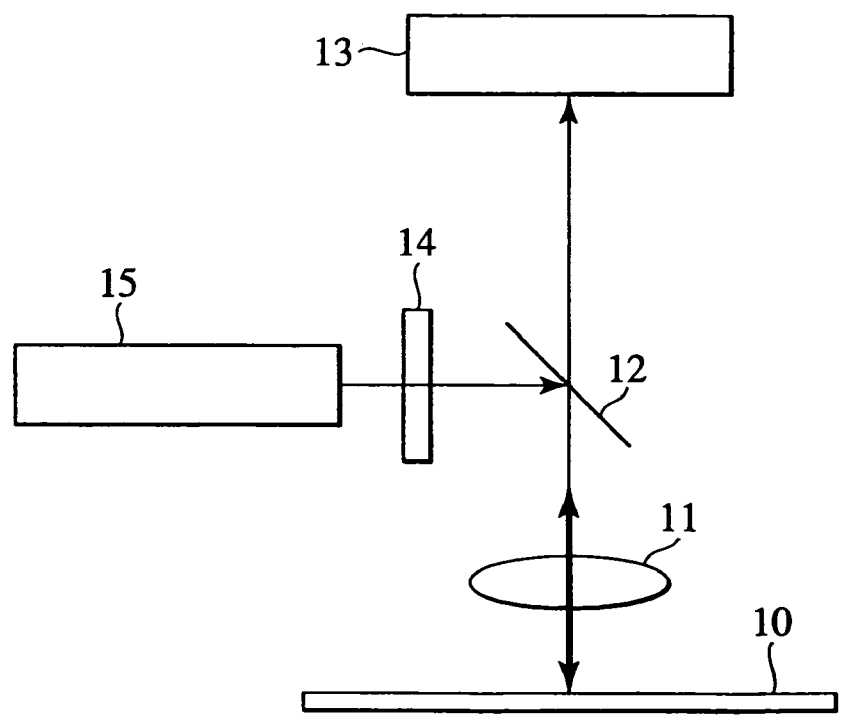
FIG. 3 is a schematic diagram for explaining a scatterometric optics system (optical measuring device)

FIG. 3 is a view explaining details of the optical shape-measuring device 16. The present embodiment is described by way of example of a scatterometry-based optical pattern shape-measuring apparatus as the optical shape-measuring device.

Light that has been emitted from a light source 15 (in the present embodiment, a Xenon lamp) is reflected by a beam splitter 12 and after being converged by an objective lens 11, irradiated onto a sample. The light, after being emitted from the light source 15, is adjusted by a filter 14 so as to have a suitable wavelength. The light, after being diffracted by the sample, is converged through the objective lens 11, then passed through the beam splitter 12, and reaches a spectroscope 13. After reaching the spectroscope 13 and being detected thereby, the light is used for the measurements described later.

Figure 24:
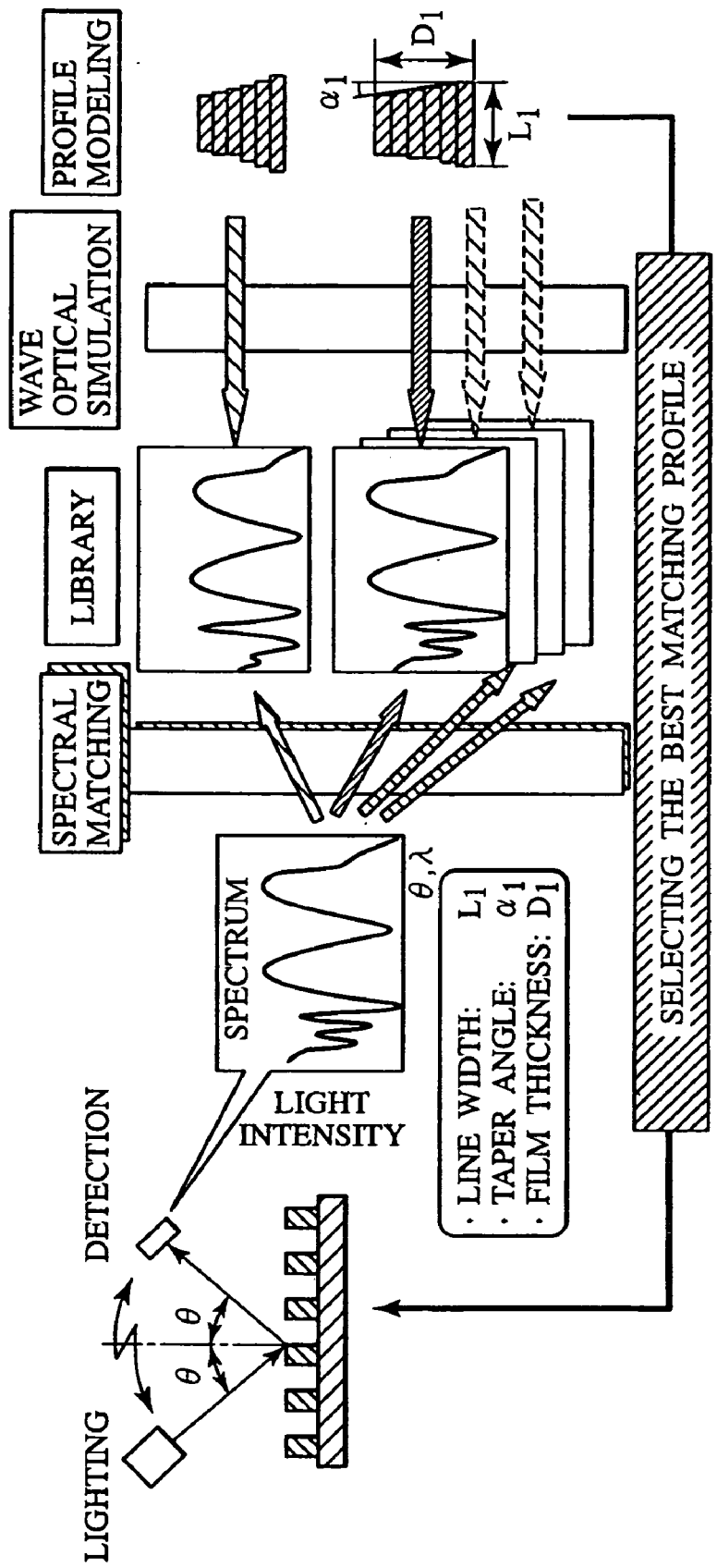
FIG. 24 is a diagram explaining the principles of operation of the optical measuring device.

The optical pattern shape measuring apparatus that uses a measuring method such as scatterometry in the present embodiment has such measuring principles as described in FIG. 24. Reflectometry, ellipsometry, the angle-resolved method, or the like is available as the foregoing measuring method.

Figure 4:
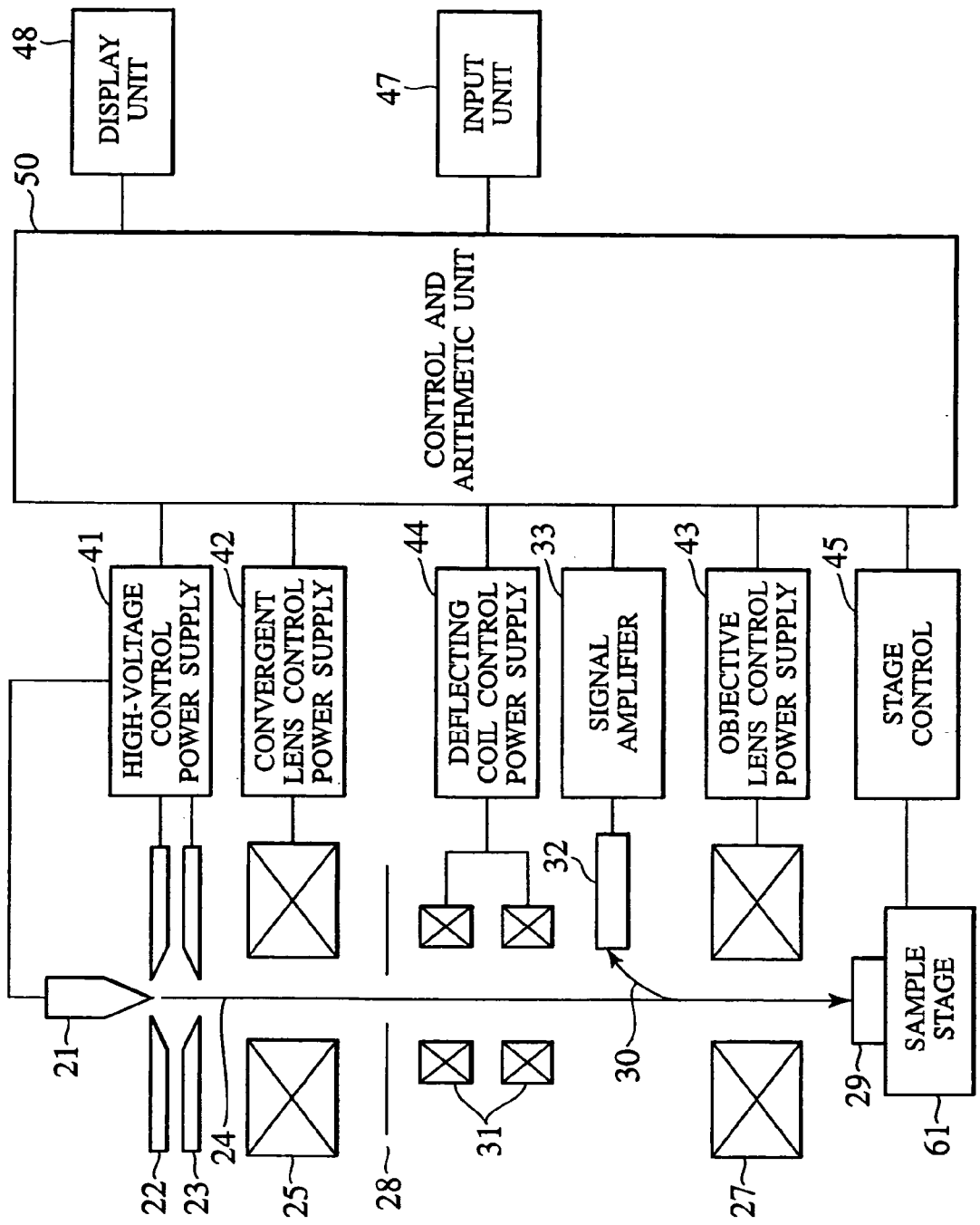
FIG. 4 is a schematic diagram of a scanning electron microscope.

FIG. 4 is a diagram for schematically explaining the scanning electron microscope. Between a cathode 21 and a first anode 22, a voltage is applied by a high-voltage control power supply 41 controlled by a control and arithmetic unit 50 (control processor), and a required emission current is induced from the cathode 21. Since an acceleration voltage is applied between the cathode 21 and a second anode 23 by the high-voltage control power supply 41 controlled by the control and arithmetic unit 50, a primary electron beam 24 emitted from the cathode 21 is accelerated and travels along optics provided at subsequent stages. The primary electron beam 24 is converged by focusing lenses 25 controlled by a focusing lens control power supply 42, and unnecessary regions of the primary electron beam 24 are removed by a diaphragm plate 28.

After this, the primary electron beam 24 is further focused onto a sample 29 as a micro spot by an objective lenses 27 controlled by an objective lens control power supply 43, and a surface of the sample is scanned in two-dimensional form by means of deflecting coils 31. A scanning signal from each of the deflecting coils is controlled by a deflecting coil control power supply 44 according to a particular observing magnification. Also, the sample 29 is fixed to a surface of a two-dimensionally movable sample stage 61. The sample stage 61 is controlled in movement by a stage controller 45.

A secondary electron 30 that has stemmed from the sample 29 by irradiation of the primary electron beam 24 is detected by a secondary electron detector 32. Thereafter, secondary signals are converted into visible signals by the control and arithmetic unit 50, at which the signals are then appropriately arrayed on another plane for control. Thus, an image corresponding to s surface shape of the sample is displayed as a sample image on a sample image display unit 48.

An input unit 47 functions as an interface between an operator and the control and arithmetic unit 50, and in addition to controlling each of the above-mentioned units via the input unit 47, the operator specifies measuring positions and issues dimension-measuring commands. The control and arithmetic unit 50 includes a memory device not shown in the figure so as to store measured length data and the like therein.

A signal that has been detected by the secondary electron detector 32 is amplified by a signal amplifier 33 and then stored into an image memory. Although the scanning electron microscope in the present embodiment includes the secondary electron detector 32, the embodiment is not limited by this configuration and a reflected-electron detector for detecting reflected electrons or a detector for detecting X-rays can also be included alternatively to or with the secondary electron detector.

Address signals corresponding to memory locations within the image memory are created inside the control and arithmetic unit 50 or inside an independently installed computer, and after being converted into analog form, the address signals are supplied to the deflecting coils 31. An X-directional address signal is a digital signal which, when the image memory has, for example, a format of 512 pixels by 512 pixels, repeatedly takes a value from 0 to 512 in order, and a Y-directional address signal is a digital signal that repeatedly takes a value of 0–512 that is incremented by 1 after the value has changed from 0 to 512 in order. These signals are converted into analog signals.

Since internal addresses of the image memory are related to addresses of the deflecting signals for scanning electron beams, a two-dimensional image of a deflecting region of the electron beam by means of scanning coils is recorded in the image memory. Signals within the image memory can be sequentially read out in chronological order via a readout address creating circuit synchronized by a readout clock. Signals that have been read out in response to addresses are converted into analog form and become brightness modulation signals of the sample image display unit 48.

The image memory has a function by which images (a plurality sets of image data) are overlapped on (combined with) one another are stored for signal-to-noise (S/N) ratio improvement. One complete image is formed by storing in overlapped form the images obtained during, for example, eight two-dimensional scans. That is to say, the images formed during one or more X-Y scans are combined to form a final image. The number of images (cumulative number of frames) for forming one complete image can be arbitrarily assigned and an appropriate value is assigned in light of conditions such as secondary-electron generating efficiency. The final image to be acquired can likewise be formed by integrating a plurality of images and then further overlapping a plurality of images on the image resulting thereby. When a desired number of images are stored or after this, information input to the image memory can also be interrupted by blanking the primary electron beam.

In addition, it may be possible to provide a sequence in which, when a ninth image is input for a setting of 8 as the cumulative number of frames, a first image will be erased and eight images will remain as a result. Alternatively, it may be possible to provide weighted addition averaging in which, when the ninth image is input, the cumulative number of images stored within the image memory is multiplied by ⅞ and then the ninth image is added to the results.

Furthermore, the scanning electron microscope in the present embodiment has a function of forming line profiles based on detected secondary electrons or backscattered electrons or the like. A line profile is formed on the basis of either the quantity of electrons detected during one-dimensional or two-dimensional scanning with a primary electron beam, or brightness information of the sample image, or the like. The thus-obtained line profile is used for purposes such as dimensional measurement of a pattern formed on, for example, a semiconductor wafer.

Dimensional measurement of a pattern is accomplished by displaying two vertical or horizontal cursor lines together with an image of a sample on the sample image display unit 48, moving the two cursors to two edges of the pattern via the input unit 47, and on the basis of image magnification information on the sample image and distance information on the two cursors, calculating measured values as dimensional values of the pattern by means of the control and arithmetic unit 50.

The description of FIG. 4 assumes that the control processor is constructed integrally with the scanning electron microscope or by analogy thereto. Of course, however, the present embodiment is not limited by such construction, and the treatment steps described below may be conducted using a control processor provided independently of the scanning electron microscope. In such a case, a transmission medium and input/output terminals are needed. The transmission medium is used to transmit the detection signal detected by the secondary electron detector 32 to the control processor or to transmit signals from the control processor to the lenses, deflector, and other sections of the scanning electron microscope. In addition, the input/output terminals are used to input/output the signals transmitted via the transmission medium. Also, a program for conducting the treatment steps described below may be registered in a memory medium beforehand and the program may be executed by means of a control processor having an image memory and supplying necessary signals to the scanning electron microscope.

The control and arithmetic unit 50 in the present embodiment assumes control relating to the optical shape-measuring device 16. However, the present embodiment is not limited by such control, and a control unit independent of the scanning electron microscope may be equipped. Also, the scanning electron microscope in the present embodiment has a function that can store a recipe defining conditions for observing a plurality of positions on, for example, a semiconductor wafer, such as measurement sections and optical conditions of the scanning electron microscope, and performing measurements and observations in accordance with the contents of the recipe.

In addition, a program for performing the treatment steps described below may be registered with a memory medium and the program may be executed by means of a control processor having an image memory and supplying necessary signals to the scanning electron microscope. In short, the below-described embodiment of the present invention is also established as a program adoptable for the charged particle beam apparatus such as the scanning electron microscope equipped with an optical shape-measuring device.

Figure 5:
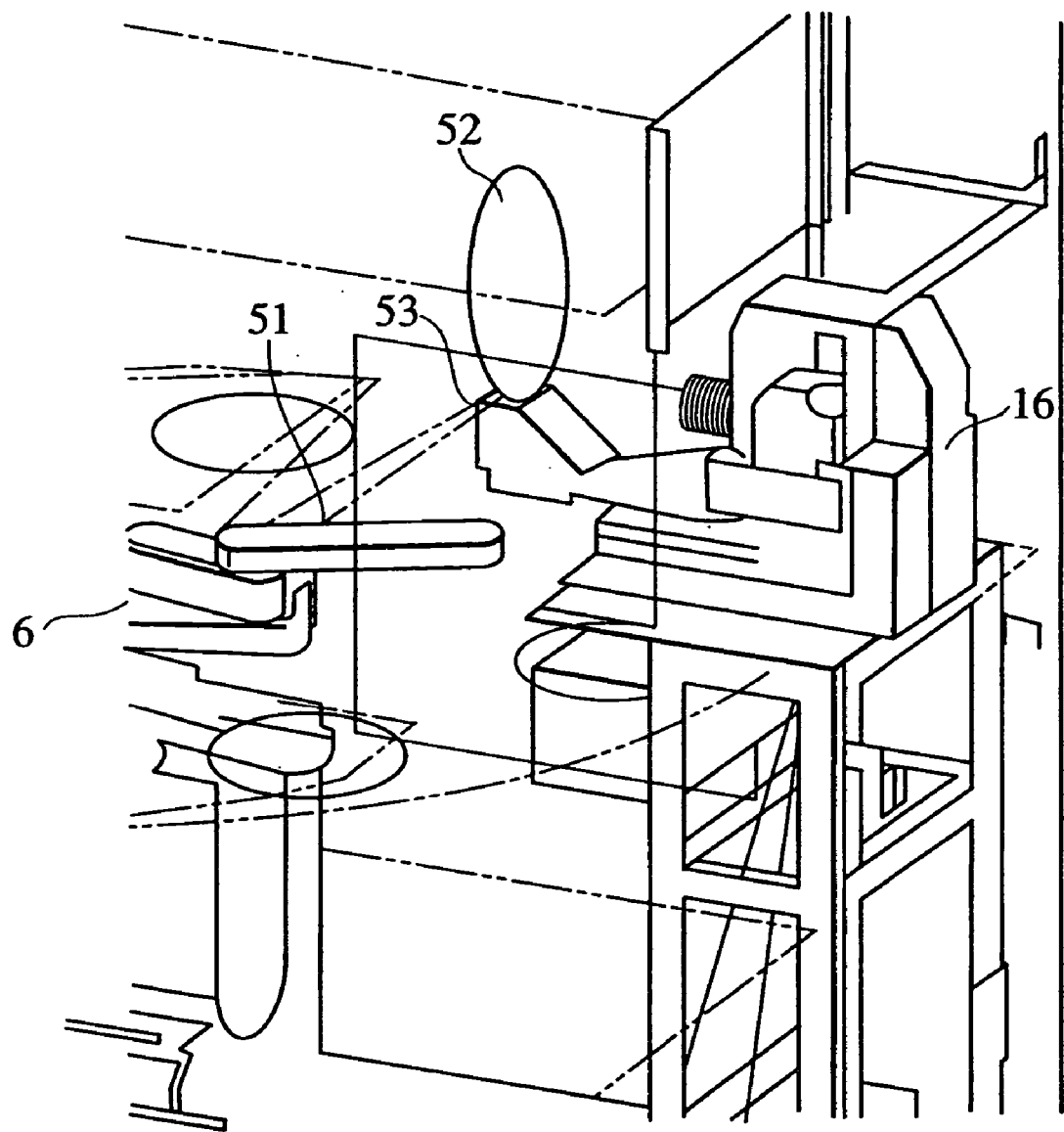
FIG. 5 is a view for explaining an example in which the optical measuring device is installed on the scanning electron microscope.

FIG. 5 is a view showing details of an optical shape-measuring device installed on the scanning electron microscope. Before or after measurement with the scanning electron microscope, a transfer arm 51 of a transfer robot 6 carries a wafer 52 to the neighborhood of an optical shape-measuring device 16 in order for this optical shape-measuring device 16 to perform measurements. The wafer 52, after being carried to the neighborhood of the optical shape-measuring device 16, is positioned under an optical axis thereof by an arm 53. The measurements described later are performed at the optical shape-measuring device 16. According to the present embodiment, the transfer robot can be shared between the CD-SEM and the optical shape-measuring device.

Embodiment 1

The present concept is intended to improve an accuracy between the two different measurement methods, but it may be applied to three dimensional measurements, and an example thereof follows.

Figure 6:
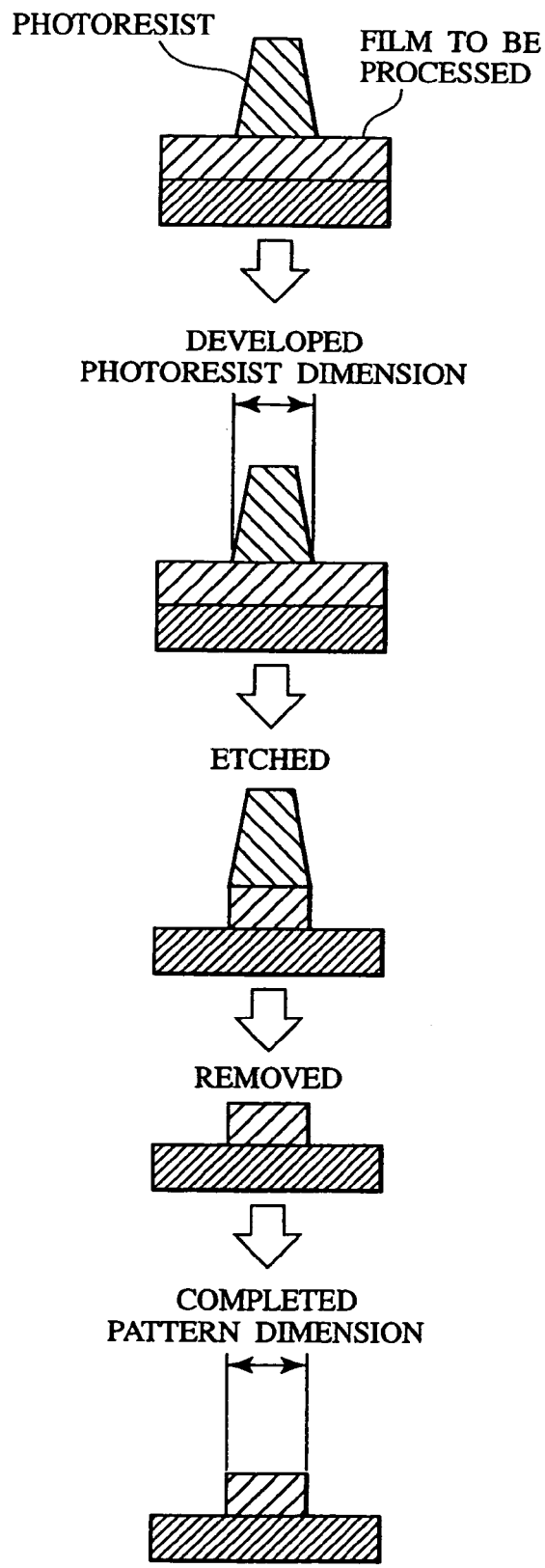
FIG. 6 is a diagram for explaining a semiconductor manufacturing process.

In a semiconductor manufacturing process, as shown in FIG. 6, after a material for forming an LSI circuit pattern has been accumulated in a film-like condition, a photoresist is applied to a surface of the materials, and the photoresist is exposed to light by an exposure device using a mask pattern manufactured to obtain a desired pattern shape. After the exposure, a developing process step is performed to remove unnecessary sections from the photoresist.

In the case of a positive resist, only exposed sections are removed by the development. In the case of a negative resist, only sections that have not been exposed are removed by the development.

In general, a formed photoresist pattern is inspected to confirm whether it stays within a desired dimension range. For the inspection, a measuring device called the CD-SEM (Critical Dimension Scanning Electron Microscope) is usually used, whereby on the basis of the image obtained when the resist pattern is observed from an upward direction, the width of the bottom of the pattern, the width of the top thereof, and the like are measured and process states are managed.

Next, etching is performed with the developed photoresist as its mask, the material itself on which a circuit pattern is to be formed is processed, and the circuit pattern is formed. After this, the photoresist that has become unnecessary is removed.

In general, similarly to measurement of the foregoing photoresist pattern dimensions, a processed pattern is inspected to confirm whether it stays within a desired dimension range. The CD-SEM is usually used for the inspection, and process steps are managed by measuring the pattern width.

In the conventional art, processes have been managed by measuring the widths of the patterns constituting the semiconductor circuit. However, since the progress of pattern-micro structuring has changed the characteristics of transistors according to the particular sectional shapes of patterns, the management of only pattern widths is insufficient to obtain desire transistor characteristics.

For example, in the process step of separating elements spatially, it is important to process the grooved section for embedding SiO2, i.e., an insulator therein, and it is said that not only the width of the groove but also the depth, taper angle, roundness-of-corner thereof affect, for example, the characteristics of a transistor.

Also, the transistor itself is doped with impurities to form a source, a drain, and channels, as its gate as a mask, so it has become clear that not only width but also the height, taper angle, and other factors of the gate itself significantly affect transistor performance.

Because of such a background, conventional management based only on pattern width has become insufficient, and instead, it has become important in recent years to manage pattern height and taper angle, i.e., the entire sectional profile shape. In the present embodiment described below, focus is placed on a dimension-measuring method and CD-SEM particularly suitable for obtaining sectional information such as pattern height and taper angle.

Figure 7:
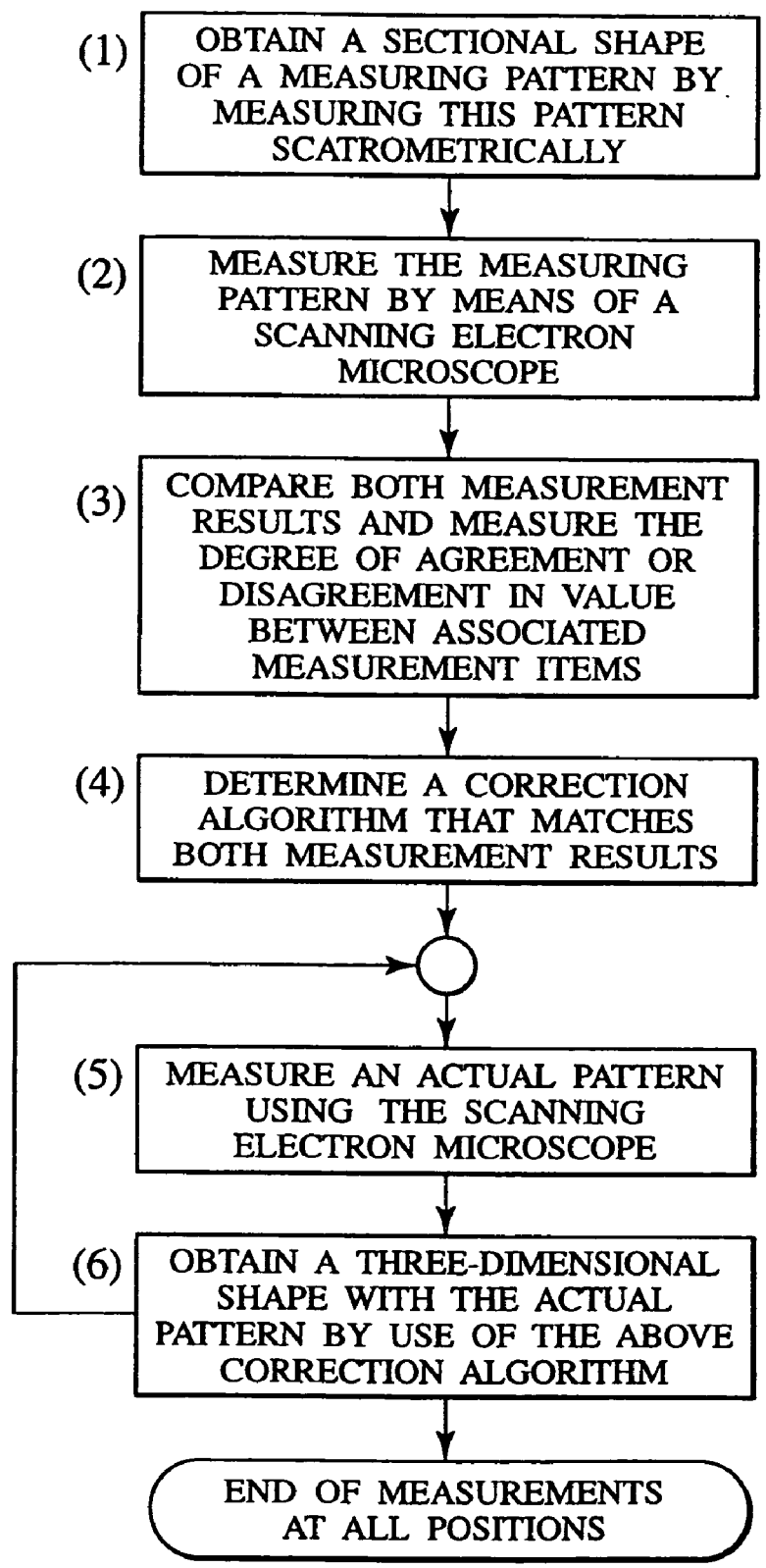
FIG. 7 is a flowchart of three-dimensional shape measurement of an actual pattern.
Figure 8:
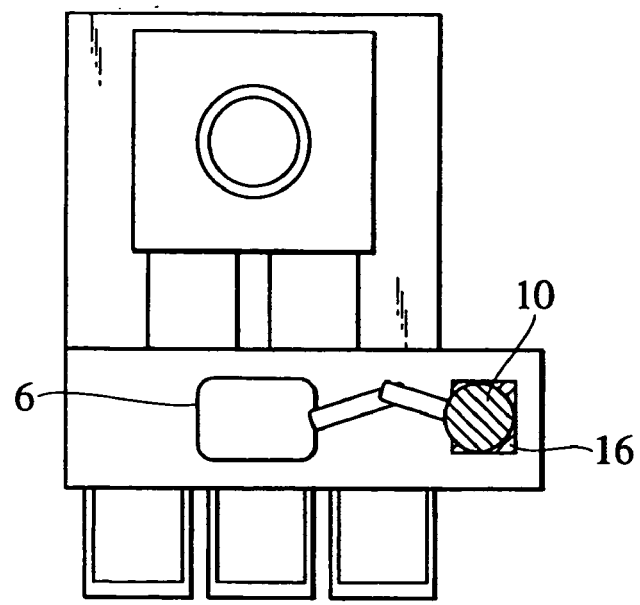
FIG. 8 is a view for explaining the disposition of a wafer for scatterometric measurement.
Figure 9:
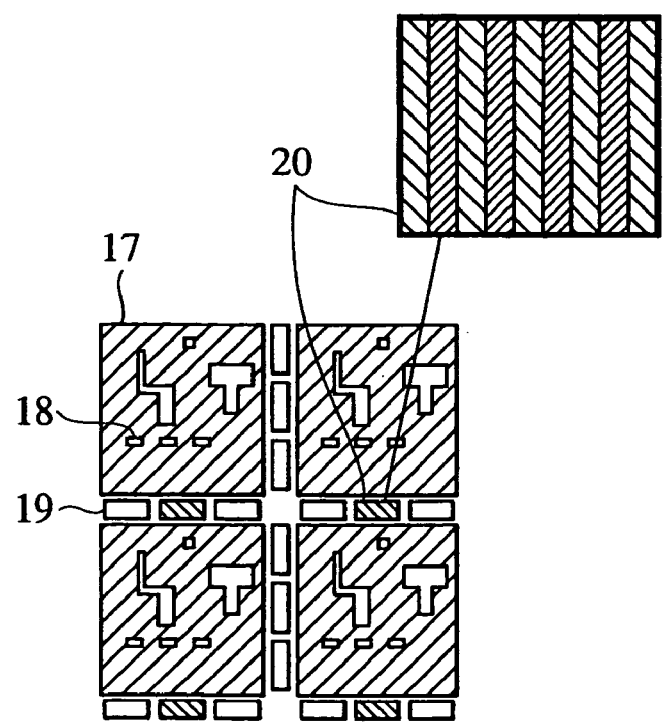
FIG. 9 is a view for explaining a measuring pattern.

An example in which an actual pattern (a pattern functioning as an on-chip circuit or formed on a chip) is measured by means of the scanning electron microscope in the present embodiment is described below using the accompanying drawings. FIG. 7 is a measuring flowchart of the present embodiment. First, as shown in FIG. 8, a wafer 10 is placed at a measuring position of an optical shape-measuring device 16 via a transfer robot 6. Next, a measurement using the optical shape-measuring device 16 is performed on a measuring pattern 20 formed on the wafer 10. This measurement is repeated for a plurality of chips. FIG. 9 is a view showing a semiconductor chip 17 formed on the wafer 10, and an actual pattern 18 is formed on the semiconductor chip 17 beforehand.

Figure 10:
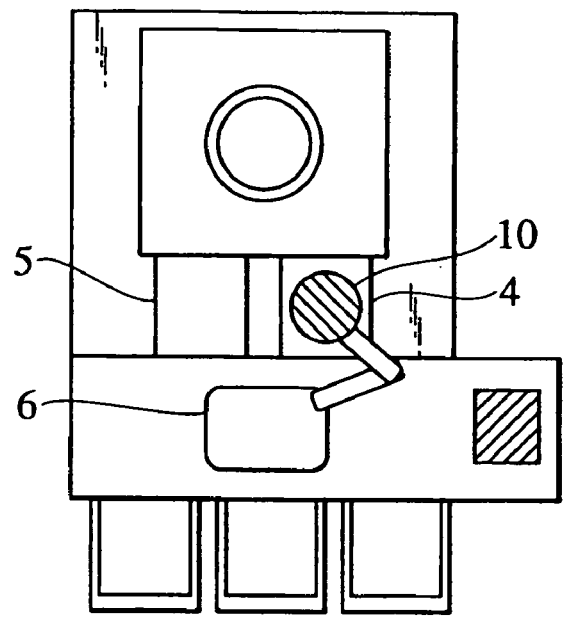
FIG. 10 is a view explaining wafer transfer to a load-lock chamber.
Figure 11:
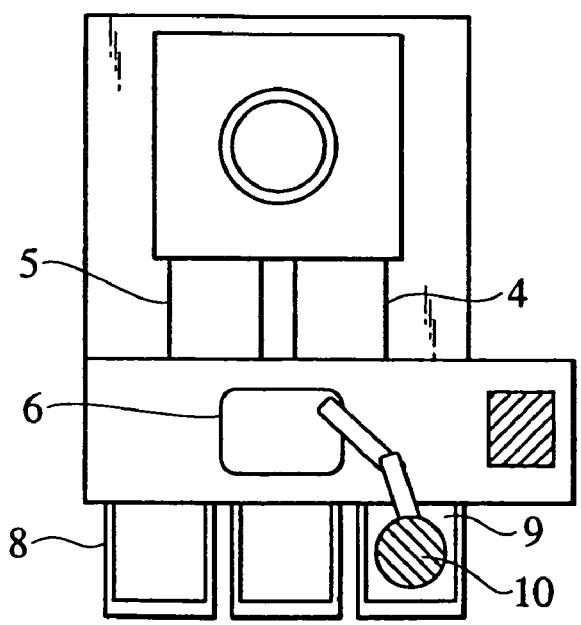
FIG. 11 is a view showing an example in which a wafer is returned to a wafer cassette.

Next, in order to perform a CD-SEM measurement on the measuring pattern 20, the transfer robot 6 transfers the wafer 10 to a load-lock chamber 4 at right (or a load-lock chamber 5 at left), as shown in FIG. 10. After this, a CD-SEM measurement is performed on the same measuring pattern 20. After the measurement, the wafer 10 is returned into a wafer cassette 9 by the transfer robot 6, as shown in FIG. 11. The CD-SEM measurement with and scatterometry-based optical pattern shape measuring apparatus measurement of one wafer are completed with the end of the successive process steps described above.

Figure 12:
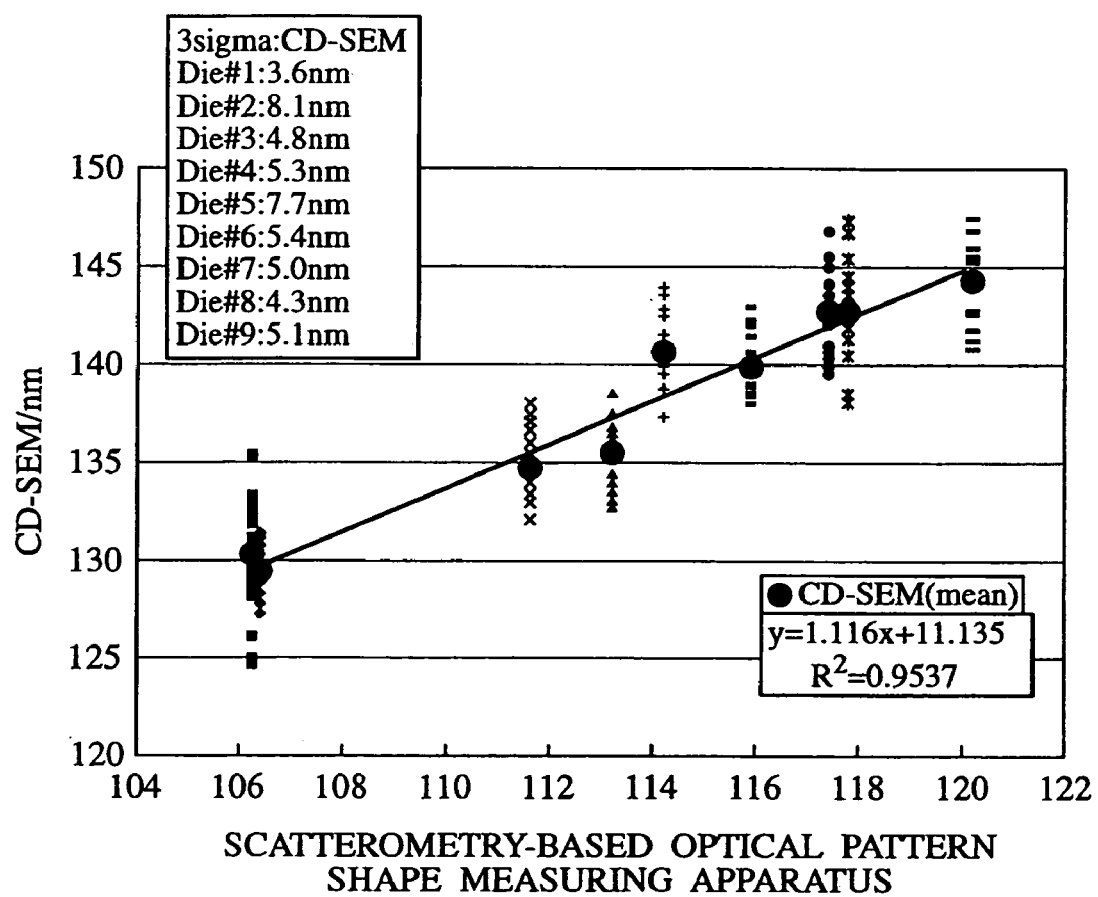
FIG. 12 is a scatter diagram for comparing the respective measurements of CD-SEM and the optical measuring device.

FIG. 12 shows an example of a scatter diagram which is prepared by picking the width values of the bottoms of patterns from the results of measurements with the CD-SEM and with the scatterometry-based optical pattern shape measuring apparatus.

The values that were measured by the scatterometry-based optical pattern shape measuring apparatus are plotted on a horizontal axis, and the values that were measured by the CD-SEM, on a vertical axis. A feature object within the measuring pattern was measured at a plurality of positions by the CD-SEM, for one value measured by the scatterometry-based optical pattern shape measuring apparatus. For this reason, average values and variations are expressed in FIG. 12.

An offset value is found for a first semiconductor wafer by calculating a difference between an average of the measurement values for the points measured by the CD-SEM and a measurement value obtained by the scatterometry-based optical pattern shape measuring apparatus in advance.

The offset value makes it possible to calculate the measurement value that would be obtained by the CD-SEM almost precisely. By calculating the offset in advance, the apparatus can estimate the measurement value of the next pattern to be measured on the same die or the same semiconductor wafer. For example, the estimated value can be used to judge whether the semiconductor wafer is good or not, to make information of a pattern section shape. And the offset value can be used to determine a permissible value for determining whether measuring by CD-SEM should be performed or not.

Figure 13:
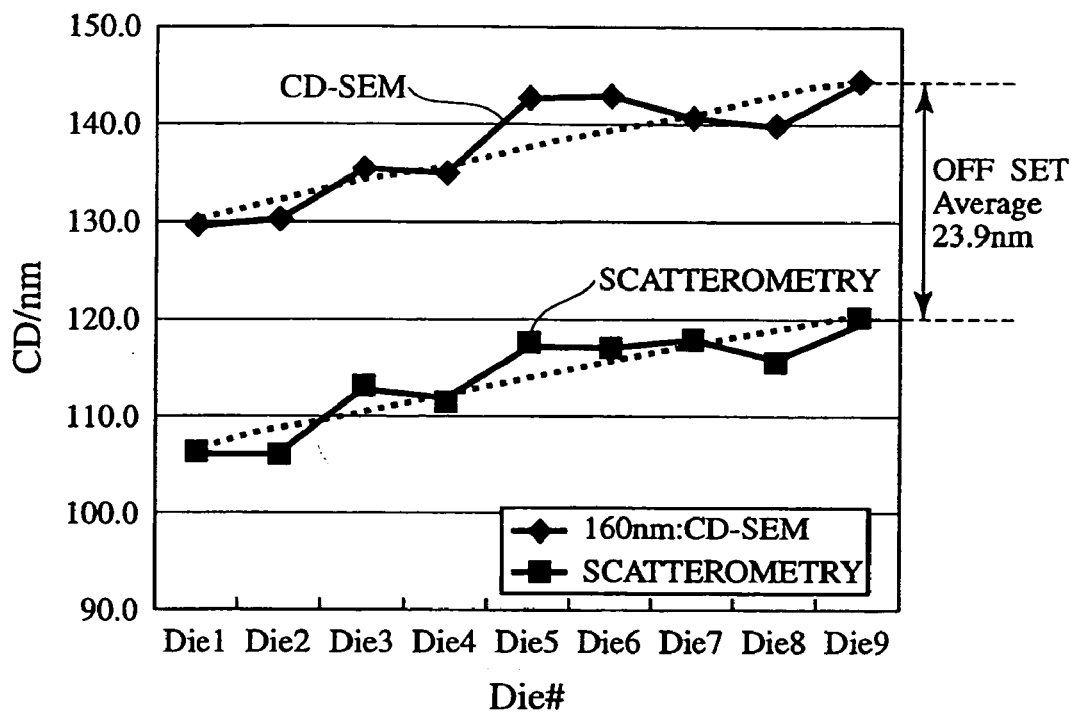
FIG. 13 is a diagram for explaining the differences between the average values of CD-SEM measurements, and the measurements of the optical measuring device.

Also, an example of plotting the widths of pattern bottoms that were measured using both is shown in FIG. 13. The data measurements with the CD-SEM are average values of the measuring pattern interior. When significant offsets are present as in this figure, correction is possible by using a linear regression formula derived from the scatter diagram of FIG. 12.

Figure 14:
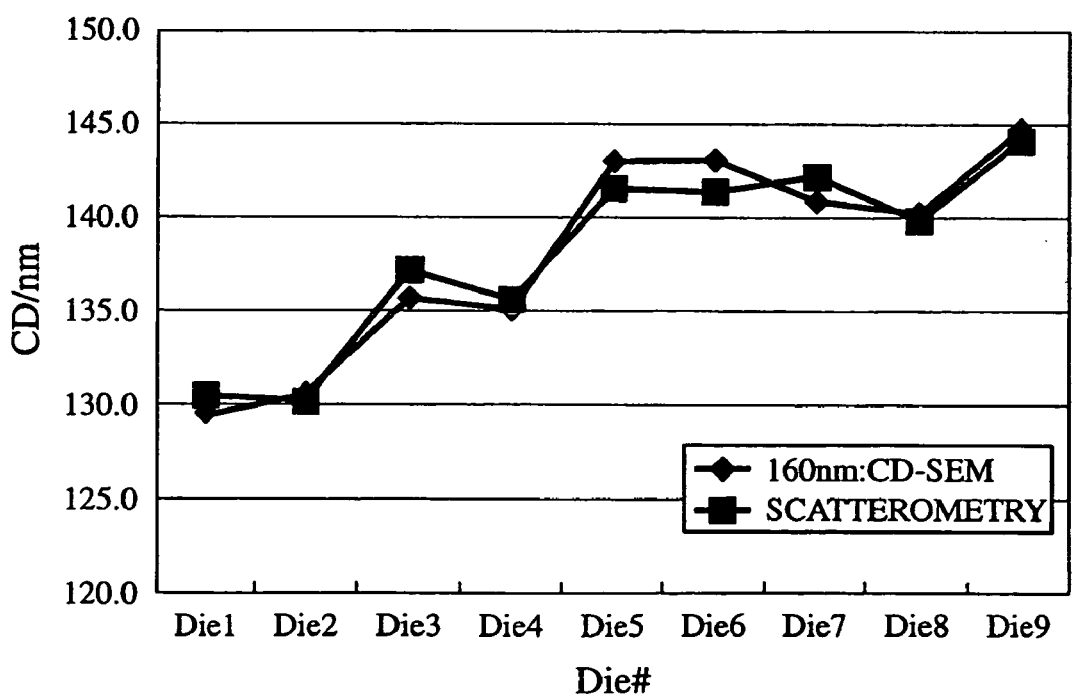
FIG. 14 is a diagram for explaining the corrected measurements of the optical measuring device.

For example, the graph shown in FIG. 14 is a case in which the values that were measured by the scatterometry-based optical pattern shape measuring apparatus are corrected on the basis of a linear regression formula. In this way, it is possible to integrate the data measurements with the scatterometry-based optical pattern shape measuring apparatus and those of the CD-SEM.

Figure 15:
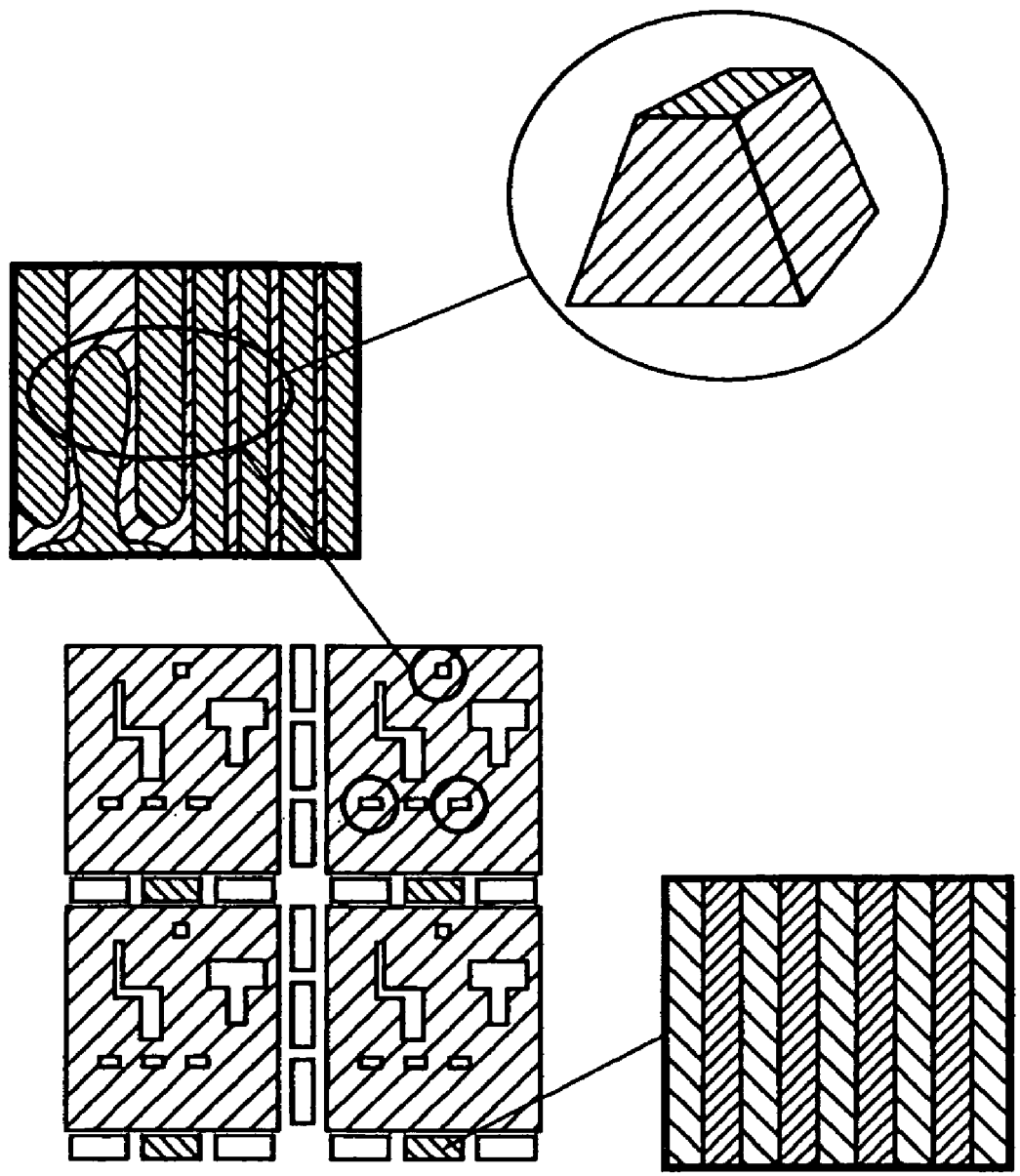
FIG. 15 is a view showing an example of the determined three-dimensional shape of a pattern.

Once it has been possible to integrate the data measurements with the scatterometry-based optical pattern shape measuring apparatus and those of the CD-SEM, it becomes possible to estimate a three-dimensional shape of an actual pattern from that of the measuring pattern, as shown in FIG. 15.

Following the above, by performing similar measurements on other wafers as well, it becomes possible to conduct the three-dimensional shape measurement of the actual pattern that has not been executable using the CD-SEM or the scatterometry-based optical pattern shape measuring apparatus alone. It is also possible, and very meaningful, to display a wafer surface internal distribution based on the thus-measured three-dimensional shape data of the actual pattern.

Figure 16:
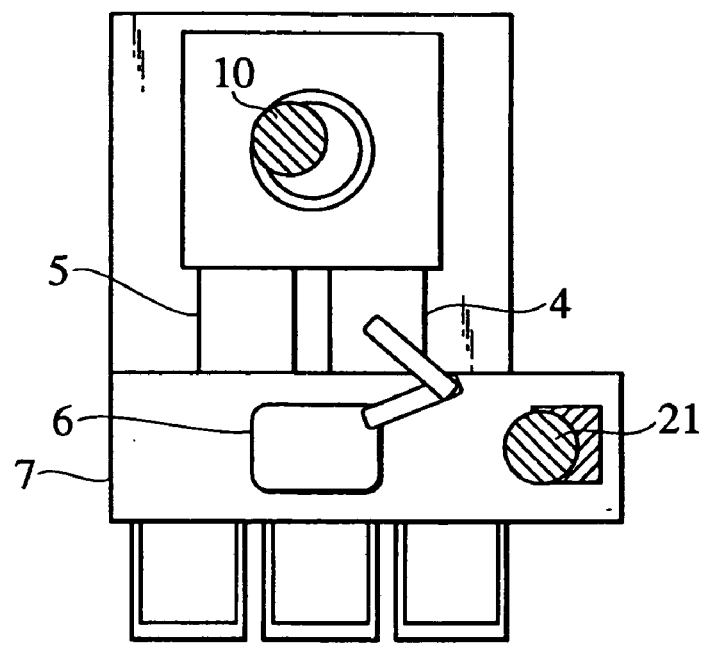
FIG. 16 is a view for explaining an example of concurrent measurement with the optical measuring device and the CD-SEM.

In addition, total throughput becomes improvable by, as shown in FIG. 16, while measuring a wafer 10 by use of the CD-SEM, measuring a wafer 21 concurrently by use of the scatterometry-based optical pattern shape measuring apparatus. Furthermore, it is also effective to allow independent measurements with the CD-SEM and the scatterometry-based optical pattern shape measuring apparatus each.

Figure 17:
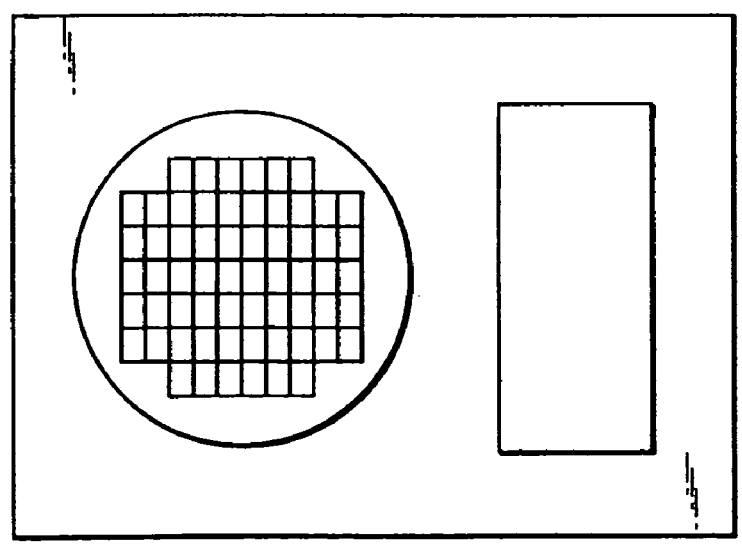
FIG. 17 is a view explaining an example of sharing a measuring recipe.

Since the same wafer is thus measured using the CD-SEM and the scatterometry-based optical pattern shape measuring apparatus, information common to respective measuring recipes, for example, such an in-wafer chip matrix as shown in FIG. 17, is always present. Therefore, the use of this integrated-type semiconductor device pattern measuring apparatus allows the use of common information, thus making it easy to create recipes.

Embodiment 2

Figure 18:
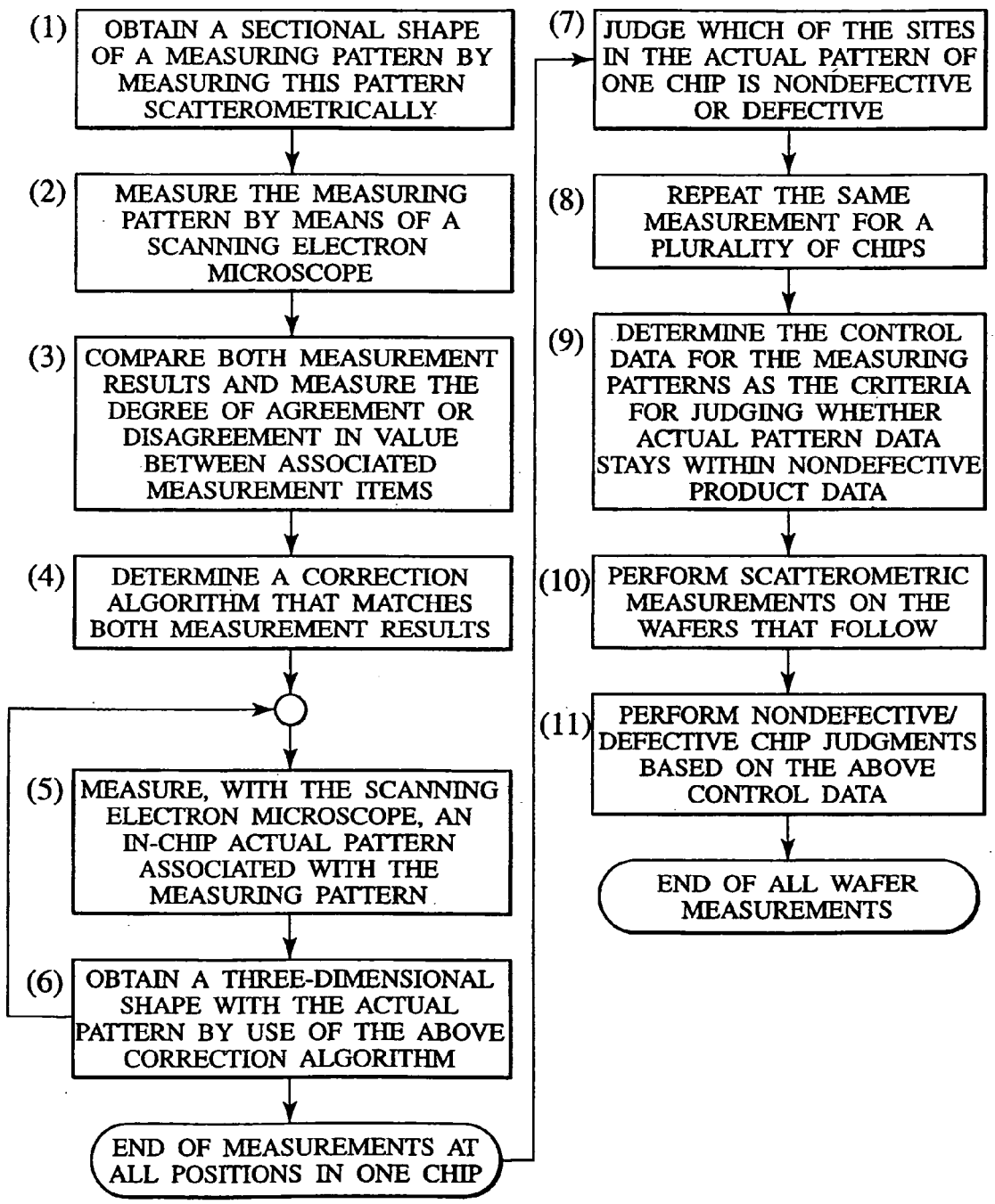
FIG. 18 is a flowchart of nondefective/defective chip judgment of an actual pattern from a measuring pattern.
Figure 19:
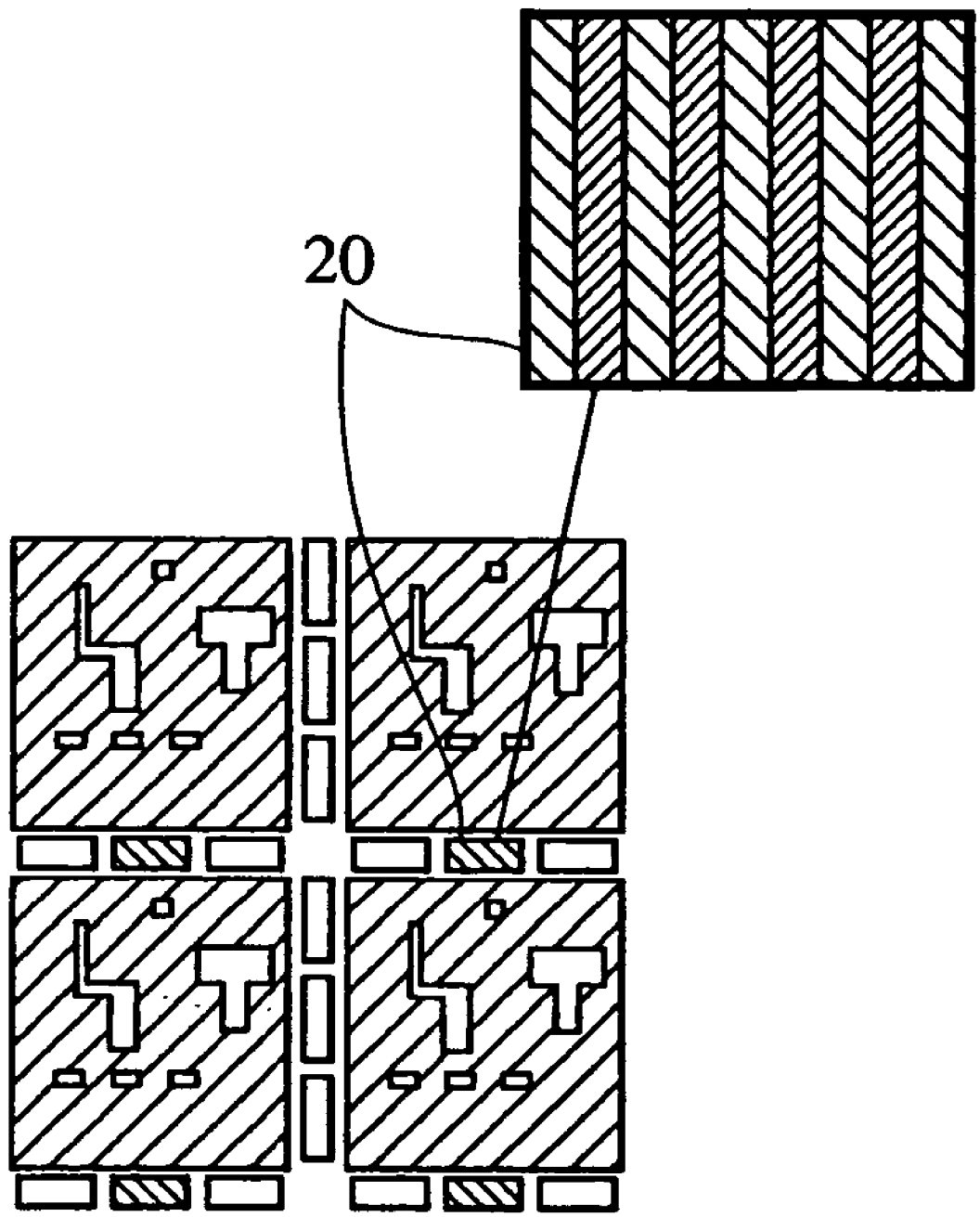
FIG. 19 is a view for explaining the measurement of the same measuring pattern.
Figure 20:
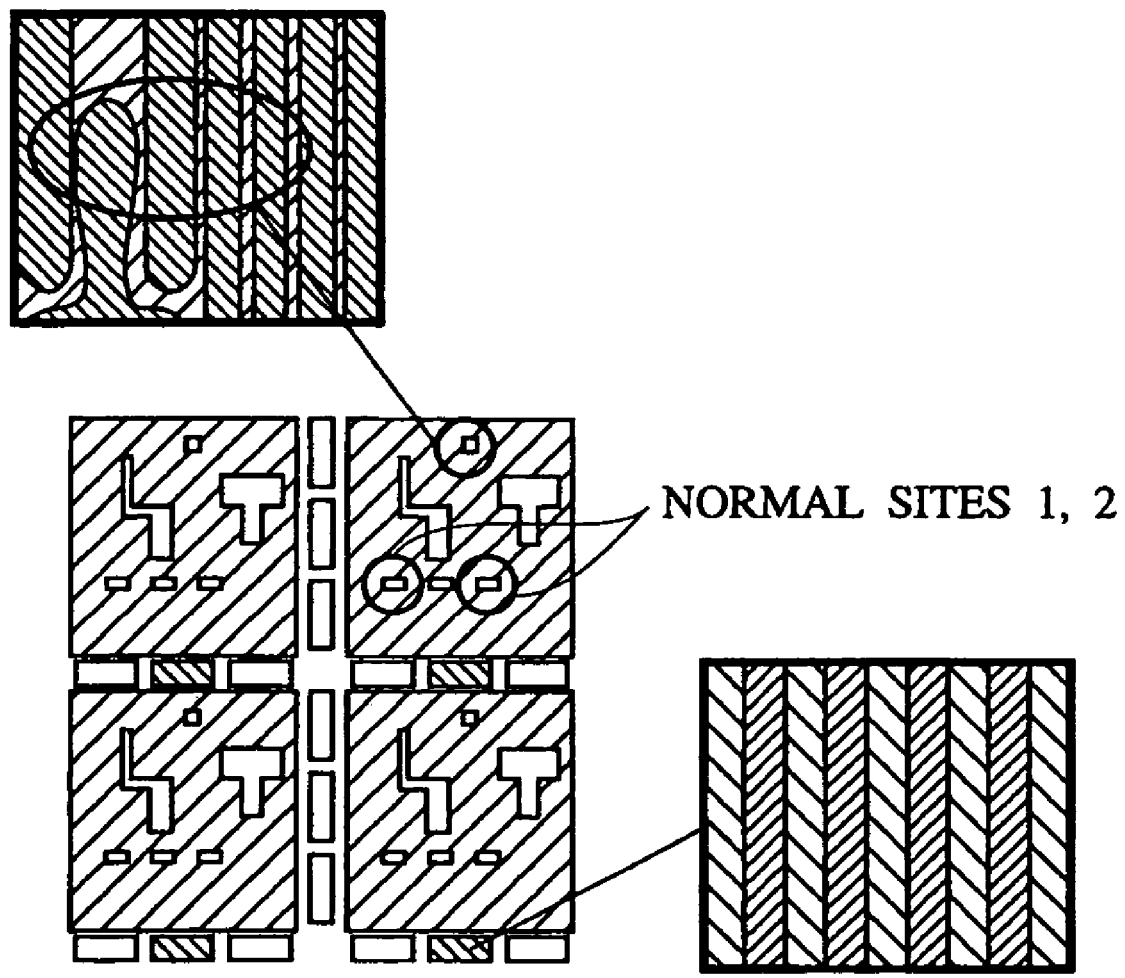
FIG. 20 is a view for explaining non defective/defective chip judgment of a pattern.
Figure 21:
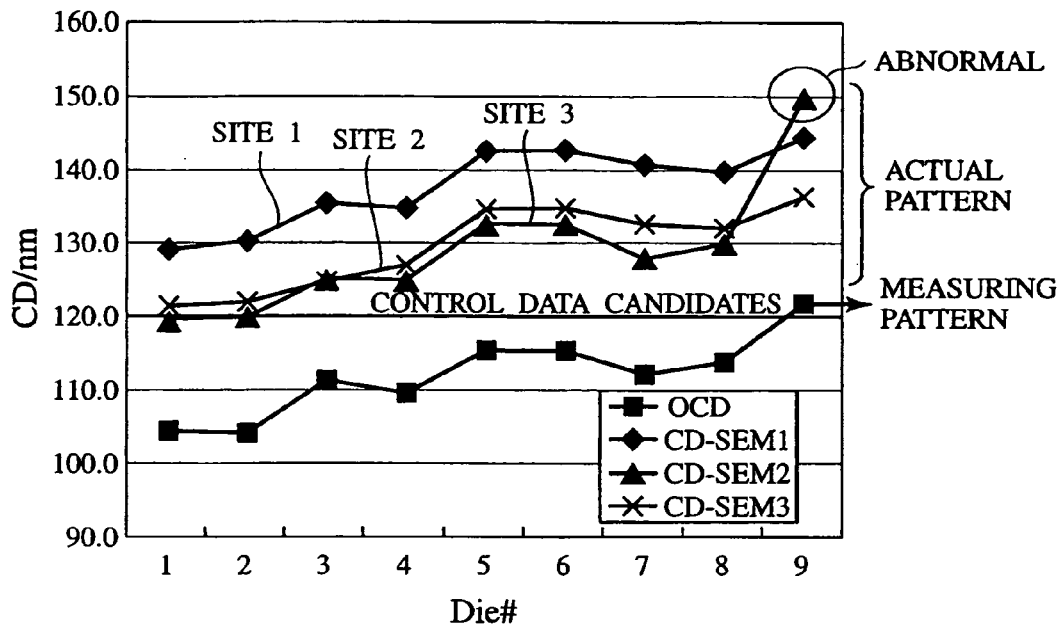
FIG. 21 is a view explaining an example of nondefective/defective chip judgment of a pattern by use of a measuring pattern.

A second embodiment is described below, in which whether an actual pattern is nondefective or defective is judged from a measuring pattern. A perspective view of an integrated-type semiconductor device pattern measuring apparatus required for the judgment is already shown in FIG. 2. A measuring flow in the second embodiment is shown in FIG. 18. The flow down to measurement of such a measuring pattern 20 as shown in FIG. 19, i.e., down to the section shown as flow step 4 in FIG. 18, is the same as for the first embodiment. Next as shown in step 5 of FIG. 18, an actual pattern within a chip that corresponds to the measuring pattern is measured using the length-measuring SEM. The way the measurement is conducted is shown in FIG. 20. In the example of this figure, the measurement is repeated at three sites in a chip, and the figure indicates that sites 1 and 2 are normal and indicates that a site 3 has the defect of short-circuiting. An example in which identification numbers of a plurality of chips on which such comparative measurements were performed are plotted on a horizontal axis is shown in shown in FIG. 21. In the case of the present embodiment, the figure implies that when the width of the measuring pattern is in excess of 120 nm, the site 3 in the actual pattern is likely to become defective, and also indicates that for this product, the particular value is one of the permissible values to be adopted as control data.

In general, since the measuring speed of the scatterometry-based optical pattern shape measuring apparatus is currently higher than that of the CD-SEM, measurements for nondefective/defective chip judgment, based on the control data mentioned above, can be performed on a greater number of chips on a greater number of wafers.

Using the calculated permissible value and the optical measurement can reduce a number of measurement points or remove the measuring by the CD-SEM. When the measurement value measured by the scatterometry-based optical pattern shape measuring apparatus is not good, as compared to the permissible value, the actual pattern is measured by the CD-SEM. Because allover measurement time by the CD-SEM can be reduced, throughput of measurement improves.

For example, if the scatterometry-based optical pattern shape measuring apparatus is outside of a vacuum chamber of CD-SEM, vacuuming times for measurements by the CD-SEM can be reduced thereby reducing total measurement time.

Furthermore, it is possible to improve the throughput by reducing a number of measurement points when the measurement value measured by the scatterometry-based optical pattern shape measuring apparatus is not good based on the permissible value. In this case, measurement time can be reduced by measuring only dies of the semiconductor wafer which have high potential for defects. For example, it can realize improvement by the measuring only measurement points which are very close to a nearby pattern and may connect to the nearby pattern.

The present embodiment produces an effect that the use of this integrated-type semiconductor device pattern measuring apparatus makes it possible to monitor the presence or absence of abnormality on a greater number of chips on a greater number of wafers.

Embodiment 3

Shown below is a third embodiment in which, when a judgment value implying that an actual pattern is likely to become defective is obtained as in the second embodiment, the number of length-measuring SEM measurement sites can be reduced by measuring all in-wafer measuring patterns by use of the scatterometry-based optical pattern shape measuring apparatus shorter in measuring time, and then performing length-measuring SEM-based measurements and observations only on the chips arranged in the measuring pattern judged to be abnormal.

Figure 22:
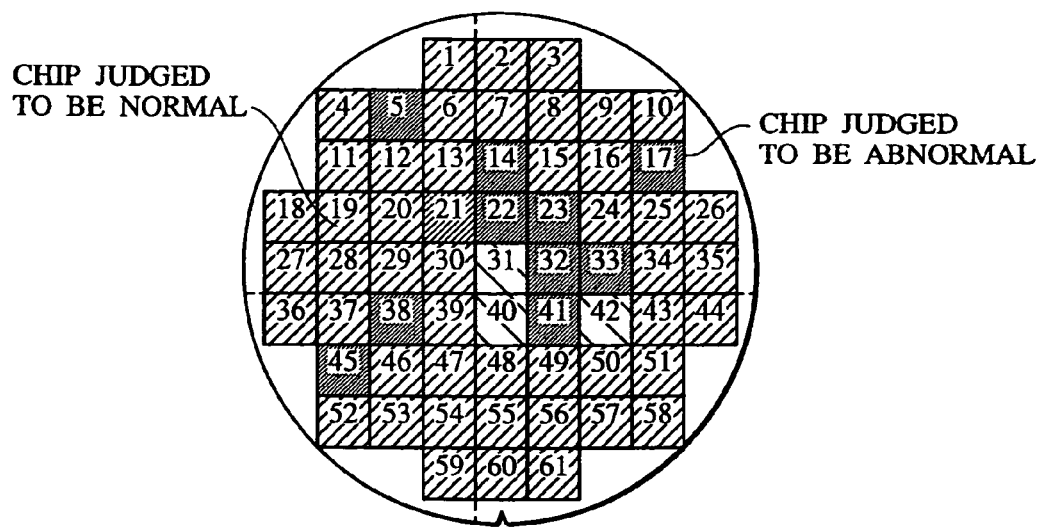
FIG. 22 is a view explaining the state of a wafer whose nondefective/defective chip judgment has been completed.
Figure 23:
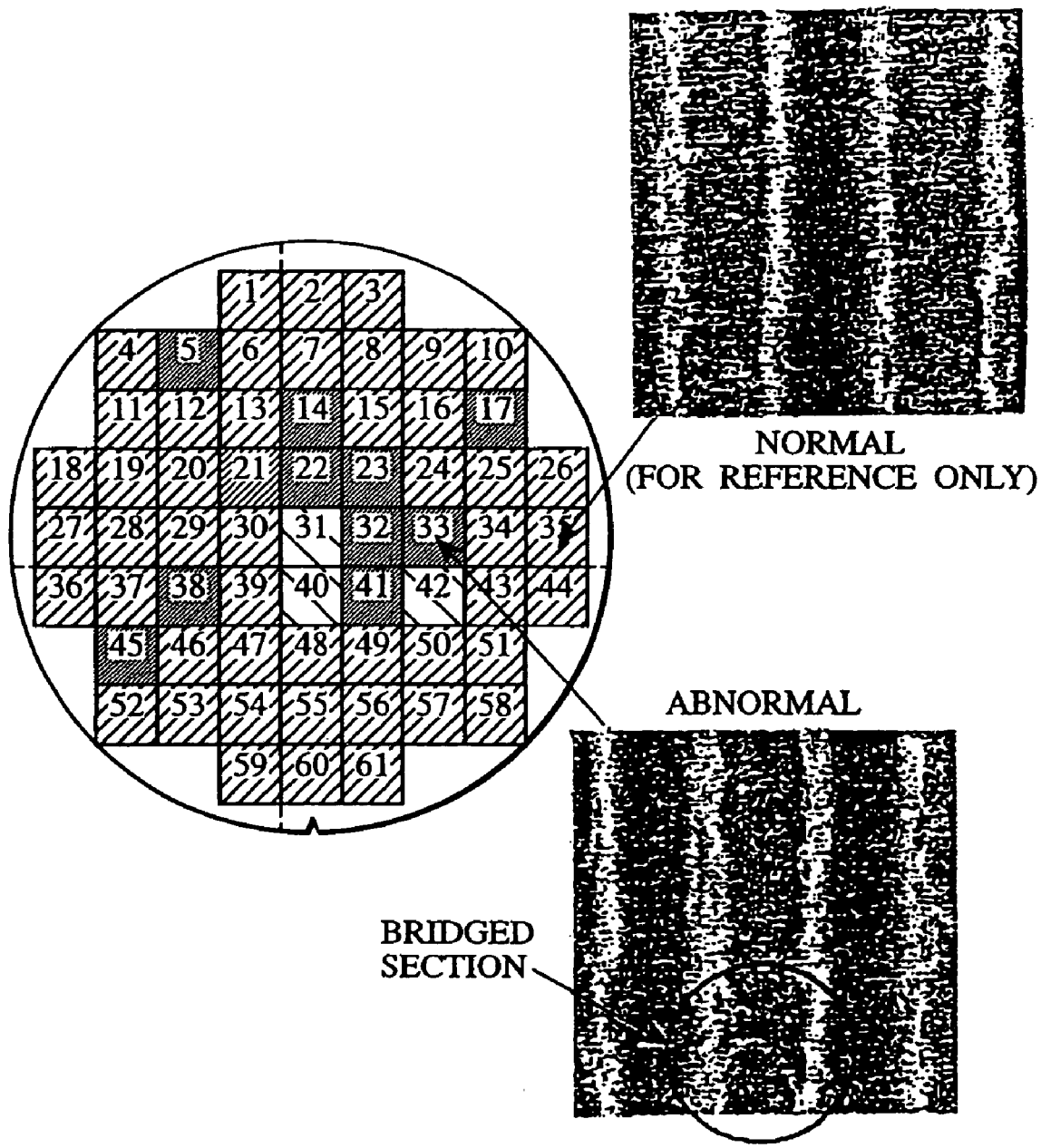
FIG. 23 is a view showing CD-SEM measurements on a chip that was judged to be abnormal.

A perspective view of an integrated-type semiconductor device pattern measuring apparatus required for implementing this embodiment is already shown in FIG. 2. Also, the step in which the measuring patterns arranged for each chip are measured with the scatterometry-based optical pattern shape measuring apparatus shorter in measuring time in order to conduct a nondefective/defective chip judgment, is already shown in the flowchart of FIG. 18. In accordance with this flowchart, length-measuring SEM measurement and observation of such an actual pattern measuring section in a previously specified chip as shown in FIG. 20 are performed on such a wafer as shown in FIG. 22. An example of a section whose abnormality was discovered as a result of the observation is shown in FIG. 23. The example shown in this figure shows a bridging defect in part of the actual pattern in the chip which was judged to be abnormal.

According to the present embodiment, after monitoring for abnormality has been conducted, the type of abnormality can also be identified within a short time by first performing SEM observations only on a chip which was found to be abnormal, and then analyzing the processing state distribution of the pattern in the wafer surface region. Thus, the results of process changes and the like can be analyzed rapidly and this contributes to reduction in semiconductor device development period.

According to the present invention, by performing measurements with both an optical shape inspection apparatus and a scanning electron microscope, it is possible to efficiently use the information obtained from both and thus improve measuring efficiency.

While the invention has been described in its preferred embodiments, it is to be understood that the words which have been used are words of description rather than limitation and that changes within the purview of the appended claims may be made without departing from the true scope and spirit of the invention in its broader aspects.

While the foregoing has described what are considered to be the best mode and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

What is claimed is:

1. A dimension-measuring method for selectively measuring a first circuit pattern of a die of a semiconductor wafer with a charged particle beam comprising;
    irradiating a light to a second pattern formed on a scribing region of the semiconductor wafer other than the first circuit pattern before loading the semiconductor wafer into a measuring chamber in which the sample would be scanned by the charged particle beam;
    measuring a dimension of the second pattern based on a reflected light from the second pattern;
    determining whether the measured dimension value of the second pattern is out of a pre-estimated range; and
    in the event the measured dimension value of the second pattern is out of the pre-estimated range, scanning the charged particle beam to the first circuit pattern for measuring a dimension of the first circuit pattern formed on the die which is surrounded by the scribing region having the second pattern determined as being out of the pre-estimated range, after loading the semiconductor wafer into the measuring chamber.

2. A charged particle beam apparatus, comprising:
    a charged particle source;
    a scanning deflector for scanning a sample with a charged particle beam emitted from said charged particle source;

an objective lens for focusing the charged particle beam on said sample;

a detector for detecting charged particles emitted from said sample;

a controller for computing a dimension of said sample on the basis of an output from said detector;

a program for execution by the controller; and an optical measuring device for irradiating said sample with light to measure a dimension thereof from the light detected by irradiation of said light on the outside of a measuring chamber in which the sample is to be scanned by the charged particle beam;

wherein execution of the program by the controller causes the apparatus to perform steps for selectively measuring a first circuit pattern of a die of a semiconductor wafer as the sample, the steps comprising:

irradiating a light to a second pattern formed on a scribing region of the semiconductor wafer other than the first circuit pattern before loading the semiconductor wafer into the measuring chamber in which the sample is to be scanned by the charged particle beam;

measuring a dimension of the second pattern based on a reflected light from the second pattern;

determining whether the measured dimension value of the second pattern is out of a pre-estimated range; and in the event the measured dimension value of the second pattern is out of the pre-estimated range, scanning the charged particle beam to the first circuit pattern for measuring a dimension of the first circuit pattern formed on the die which is surrounded by the scribing region having the second pattern determined as being out of the pre-estimated range, after loading the semiconductor wafer into the measuring chamber.

\* \* \* \* \*